United States Patent [19]

Tolbert et al.

[11] 4,187,149
[45] Feb. 5, 1980

[54] CELL CULTURE SAMPLING SYSTEM

[75] Inventors: William R. Tolbert, Manchester; Joseph Feder, University City, both of Mo.

[73] Assignee: Monsanto Company, St. Louis, Mo.

[21] Appl. No.: 881,458

[22] Filed: Feb. 27, 1978

[51] Int. Cl.$^2$ .............................................. C12B 1/00
[52] U.S. Cl. ................. 195/104; 128/214 R; 215/247; 215/249
[58] Field of Search ................ 195/127, 104, 103.5 R, 195/121, 126, 1.7, 1.8; 215/247, 249; 128/214 R

[56] References Cited

U.S. PATENT DOCUMENTS

| | | | |
|---|---|---|---|
| 2,364,126 | 12/1944 | Cantor et al. | 215/247 |
| 3,013,687 | 12/1961 | Gould | 215/249 |
| 3,017,050 | 1/1962 | Barr, Sr. et al. | 215/247 |
| 3,075,888 | 1/1963 | Achorn et al. | 195/127 |
| 3,092,278 | 6/1963 | Yarnhall | 215/247 |
| 3,424,329 | 1/1969 | Hershberg et al. | 215/247 |
| 3,547,297 | 12/1970 | Herbert et al. | 215/46 |
| 3,587,897 | 6/1971 | Rohde | 215/46 X |
| 3,793,154 | 2/1974 | Efthymiou | 195/139 |
| 3,850,748 | 11/1974 | Cook et al. | 195/1.8 |
| 4,084,718 | 4/1978 | Wadsworth | 215/247 |
| 4,121,585 | 10/1978 | Becker, Jr. | 128/214 R |

OTHER PUBLICATIONS

D. J. D. Hockenkull, Progress in Industrial Microbiology, vol. 2, Interscience Publishers, 1960, pp. 105-130.
J. Daniel Lynn and Ronald T. Acton, Biotechnology and Bioengineering, vol. XVII, 1975, pp. 659-673.

*Primary Examiner*—Alvin E. Tanenholtz
*Assistant Examiner*—Robert J. Warden
*Attorney, Agent, or Firm*—Scott J. Meyer; James W. Williams, Jr.

[57] ABSTRACT

A cell culture sampling device is provided which comprises a double septum holder having an axial bore therethrough, upper and lower septa retaining members, said upper retaining member having lip means to retain immobilized an external septum and said lower retaining member having shoulder means to retain immobilized an internal septum, said lip and shoulder means being spaced apart to thereby define a fixed chamber between said immobilized septa.

9 Claims, 2 Drawing Figures

CELL CULTURE SAMPLING SYSTEM

BACKGROUND OF THE INVENTION

This invention relates to a method and device for cell culture sampling in suspension cell culture vessels.

The in vitro growth of animal cells as cell cultures is a widely developed art. In recent years there has been a trend in the cell culture field toward growing these cells in suspension culture. Background information on this trend can be had be reference to U.S. Pat. No. 3,850,748 and references cited therein.

For a variety of reasons, there is a need to take frequent cell culture samplings during growth of animal cells in suspension culture. Various parameters of the cell culture growth conditions need to be monitored such as, for example, determination of the condition of the cells and the culture medium components, estimation of the cell density, and assay of products being released into the culture medium. Similar samplings need to be made during storage of cell culture media to ensure the integrity of the media.

Critical to any cell culture system is the maintenance of absolute sterility. Since the taking of samples from cell culture vessels provides an ideal source of microbial contamination, special precautions must be observed during any sampling procedure. A common method of attacking the problem of microbial contamination is to employ high levels of antibiotics in the cell culture medium. The use of antibiotics, however, detrimentally affects cell metabolism and cell products by masking chronic low level contamination, by stimulating the development of resistant microorganisms and by introducing uncontrolled variables into the cell culture process. Consequently, a method of sampling which can be carried out without need to employ antibiotics in the culture medium would have much practical use.

Another approach used for maintaining a sterile environment during cell culture sampling is to carry out the sampling procedure in a biological laminar flow hood. However, this means is useful only for relatively small vessels and is not adaptable to large scale culture vessels.

Sampling procedures used in the microbiological fermentation field have also been adapted for use in cell culture system. In the fermentation field, sampling techniques have been developed in which the sample is withdrawn with a sterile hypodermic needle inserted through a pierceable and self-resealable, elastomeric septum in an appropriately placed sampling port of the fermentation vessel. Such techniques are illustrated, for example, in U.S. Pat. No. 3,075,888. However, this technique is suitable for piercing at each hole only once and is not generally adaptable to repeated samplings in cell culture systems. The inherent risk in repeated use of such procedures in the cell culture field is apparent from the fact that a mammaliam cell culture contaminated by even a single microorganism may be rapidly overgrown and destroyed since the doubling times for mammalian cells are from 50 to 500 times larger than for common microorganisms. This cell culture contamination problem differs significantly from what occurs in the ordinary fermentation field where the proliferation rate of likely microbial contaminants is on the same order as that of the desired culture. A single or even a few contaminating microorganisms do not overgrow the desired fermentation culture and thus are not observed.

BRIEF DESCRIPTION OF THE INVENTION

In accordance with the present invention a cell culture sampling device is provided which comprises a double septum holder having an axial bore therethrough, an upper septum retaining member, and a lower septum retaining member, said upper retaining member having lip means to retain immobilized an external septum, said lower retaining member having shoulder means to retain immobilized an internal septum, said lip and shoulder means being spaced apart to thereby define a fixed chamber between said immobilized septa. This fixed chamber provides an air space which prevents any liquid from the needle tip from forming a continuous path in the device as the needle is drawn through the septa during the sampling operation. The invention thereby prevents mobile microorganisms from penetrating the seal along such a liquid path during the sampling method.

DETAILED DESCRIPTION OF THE INVENTION

Figure 1:
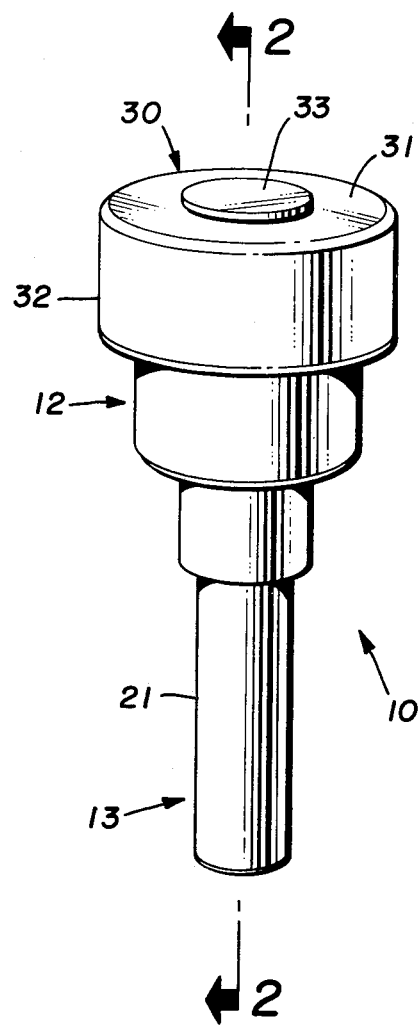

While the specification concludes with claims particularly pointing out and distinctly claiming the subject matter regarded as forming the present invention, it is believed that the invention will be better understood from the following exemplary description taken in connection with the accompanying drawings in which FIG. 1 is a perspective view of the assembled double septum holder sampling device of this invention.

Figure 2:
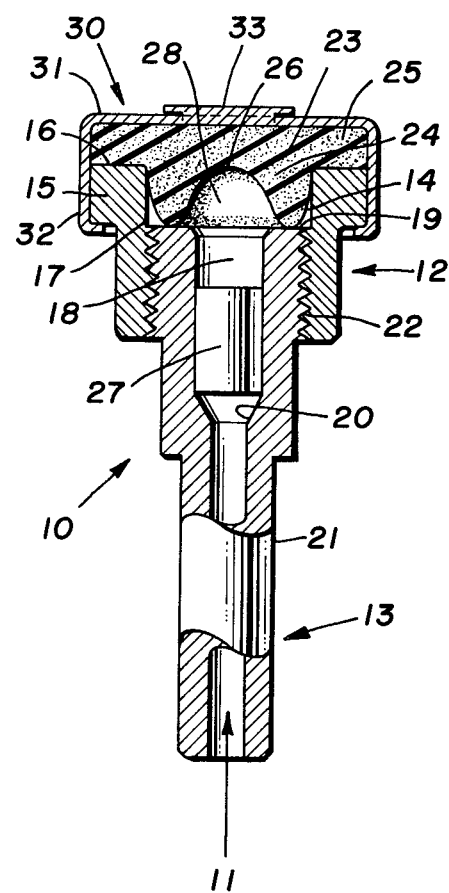

FIG. 2 is a side elevational view of the double septum holder sampling device in cross-section taken along the line 2—2 of FIG. 1.

In the drawings, reference numeral 10 designates a generally cylindrical double septum holder having an axial bore 11, upper septum retaining member 12 and a lower septum retaining member 13. The upper retaining member has a mouth 14, a peripherally flanged top part 15, a lip portion 16 and an internally threaded wall 17 at the bottom. The lower retaining member has a mouth 18, a lip portion 19, an internal shoulder 20, a stem portion 21 at the bottom and an externally-threaded wall 22 at the top. These oppositely disposed threaded walls are adapted for coupling together. The upper and lower retaining members are preferably made of stainless steel or other such sterilizable materials which are non-toxic to cells and cell culture media.

The mouth in upper retaining member 12 is adapted to accommodate a septum 23. Septum 23 is a pierceable self-resealable, elastomeric stopper which preferably has a plug portion 24 adaptable to snuggly fit in mouth 14, a peripherally flanged portion 25 which seats against lip 16 of the upper retaining member and a thin-walled center portion 26 which can be pierced with a pointed instrument such as a hypodermic needle. The septa can be fabricated from an elastomeric material such as, for example, silicone rubber, butyl rubber or a fluorinated elastomer.

The mouth 18 in lower retaining member 13 is adapted to snuggly accommodate a cylindrical septum 27 which similarly has a pierceable, self-reseable elastomeric structure. Septum 27 can be press fitted into position through the mounth of the lower retaining member. Shoulder 20 constricts mouth 18 above the stem portion 21 and thereby facilitates the retention of septum 27 in a fixed or immobilized position within the lower retaining member. Other shoulder means such as an annular ridge or a conical narrowing of the axial bore can be used instead of the illustrated shoulder 20. Septa 23 and 27 are thus spaced apart whereby they define a completely enclosed, fixed chamber 28. This chamber provides an air space which prevents any liquid from the needle tip from forming a continuous path as the needle is withdrawn through the septa during the sampling operation.

It will be appreciated that the specific configuration and dimensions of the chamber can vary considerably and will depend, in part, on the structure of the cell culture vessel and sampling port and the relative size of the needle used for the sampling. For example, with a sampling device as illustrated in FIGS. 1 and 2 and adapted for use in an ordinary 100 liter cell culture vessel, use of a standard hypodermic needle ranging in size from about 25 gauge ×⅝ inch long to about 20 gauge ×1½ inches long is eminently suitable (or equivalent to about 2–4 cm in round numbers on the metric scale). With use of such needles, the distance between the septa preferably ranges from about 1/32 inch to about ⅜ inch and most preferably about 5/32 inch (or equivalent to about 1–15 mm and most preferably about 5 mm in round numbers on the metric scale). In general, the smaller the needle, the smaller the distance between septa which can be used. This distance need only be sufficient to prevent liquid from the needle tip from forming a continuous path as it is withdrawn through the septa during the sampling.

The double septum holder sampling device is adapted to be covered with a cap 30 of generally cup-shaped form made, for example, from a sheet of aluminum, having a top 31 and a depending skirt 32. The terminal edge of the skirt is adapted to be crimped under the flanged top part of the upper retaining member to secure the cap over the stopper. This cap preferably has a tear tab center portion 33 which is removable to provide needle access to the septa. The remaining annular portion of the cap and the depending skirt will continue to compress the external septum in an immobilized position. U.S. Pat. Nos. 3,547,297 and 3,587,897 are illustrative of such types of caps.

The double septum holder sampling device of this invention is adapted for fluid communication with the contents of a cell culture vessel by suitable coupling at the stem portion 21 of the lower retaining member. This coupling can be made, for example, with an ordinary Swagelok ® union, to the inside sterile volume of the cell culture vessel by a tube to the desired sampling depth or directly into the side of the culture vessel at the sampling position. Thus, the terms upper and lower, top and bottom are only relative terms used for convenience in describing the device but do not fix the absolute position of various features in actual use of the device.

The upper and lower retaining members are adapted for coupling at the correspondingly opposed threaded walls 17 and 22. When the two members are tightly fastened together, the plug portion 24 of the stopper is compressed into a sealing position with the lip portion 19 of the lower retaining member to thereby provide an absolute seal between the vessel contents and the exterior atmosphere. The two retaining members are also thus adapted to be readily taken apart for ease of cleaning and replacement of septa, and for providing a loosely fitted connection for pressure relief during sterilization of the device.

In use, the double septum holder is first fully sterilized while in place in the cell culture vessel such as by autoclaving at about 250° F. (equivalent to about 125° C.) for about one to two hours or by steam sterilizing in place. The upper and lower septa retaining members are loosely connected in position during the sterilizing treatment and tightened together thereafter. Prior to the first sampling operation, the tear tab portion of the aluminum seal cap is removed, thus exposing the external septum to the outer atmosphere. The external septum is flame sterilized at about 500 to 1500° C. for a few seconds. for example, about 6 to 10 seconds, to provide a surface which is free from all viable microorganisms and spores. Samples are then withdrawn from the cell culture vessel by penetrating both septa with a sterile hypodermic needle. Following withdrawal of the sample, the external septum is again flame sterilized. The internal septum which is sterilized initially with the vessel remains sterile throughout multiple samplings without any further treatment, and the sampling method can be repeated as often as desired. The internal septum remains in a sterile environment protected by the external septum.

In actual practice, a single cell culture vessel port fitted with one of the foregoing double septum holder devices has been sampled more than 50 times without causing any problems of microbial contamination and without any antibiotics being present in the cell culture medium. Cell growth in 100 liter cell culture vessels also has been similarly continuously maintained for over 30 days with daily samplings. The double septum holder also has been used on storage vessels holding a combined total of more than 12,000 liters of cell culture media in individual 100 liter vessels for periods ranging from about one week to over 30 days with periodic sampling, again without use of antibiotics and without producing any microbial contamination during the storage period.

It will be appreciated that various adaptations and modifications of the invention can be devised by the person skilled in the art after reading the foregoing specification without departing from the spirit and scope of the invention. All such adaptations and modifications are included within the scope of the appended claims.

What is claimed is:

1. A cell culture sampling device for withdrawing samples therethrough which comprises a double septum holder having an axial bore therethrough, an upper septum retaining member and a lower septum retaining member, said upper retaining member having lip means to retain immobilized an external septum and said lower retaining member having shoulder means to retain immobilized an internal septum, said lip and shoulder means being spaced apart to thereby define a fixed chamber between said immobilized septa.

2. The sampling device of claim 1 in which said upper retaining member has an annular flange at the top.

3. The sampling device of claim 1 including a pair of pierceable, self-resealable elastomeric septa which are immobilized in said bore at opposite ends of said fixed chamber.

4. The sampling device of claim 3 in which one of said septa is a stopper having a plug portion adapted to snuggly fit in an opening at the top of the upper retaining member, a peripherally flanged portion adapted for seating on the lip portion of said upper retaining member and a thin-walled center portion adapted for piercing with a pointed instrument, and in which the other septum is a cylinder adapted to snuggly fit in an opening at the top of the lower retaining member and adapted for piercing with said pointed instrument.

5. The sampling device of claim 3 in which said upper retaining member has an annular flange at the top.

6. The sampling device of claim 5 including a metal cup-shaped cap having a top portion and a depending skirt, the terminal edge of said skirt being crimped under said annular flange.

7. The sampling device of claim 4 in which said upper and lower retaining members have oppositely disposed threaded walls adapted for coupling together.

8. The sampling device of claim 1 in which said upper and lower retaining members have oppositely disposed threaded walls adapted for coupling together.

9. The method of cell culture sampling comprising withdrawing a sample from a cell culture vessel with a hypodermic needle through a cell culture sampling device which comprises a double septum holder having an axial bore therethrough, an upper septum retaining member and a lower septum retaining member, said upper retaining member having lip means to retain immobilized an external septum and said lower retaining member having shoulder means to retain immobilized an internal septum, said lip and shoulder means being spaced apart to thereby define a fixed chamber between said immobilized septa, whereby any liquid from the tip of said needle is prevented from forming a continuous path in said device as the needle is drawn through said septa during the sampling operation.

* * * * *